United States Patent
Osman et al.

(10) Patent No.: US 8,337,544 B2
(45) Date of Patent: Dec. 25, 2012

(54) ENDOPROSTHESIS HAVING FLEXIBLE CONNECTORS

(75) Inventors: Karim S. Osman, Mountain View, CA (US); Richard R. Newhauser, Redwood City, CA (US)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 610 days.

(21) Appl. No.: 11/961,384

(22) Filed: Dec. 20, 2007

(65) Prior Publication Data

US 2009/0163992 A1 Jun. 25, 2009

(51) Int. Cl.
*A61F 2/06* (2006.01)

(52) U.S. Cl. ............. 623/1.15; 623/1.16; 623/1.18; 623/1.2

(58) Field of Classification Search ............. 623/1.16, 623/1.17, 1.18, 1.15
See application file for complete search history.

(56) References Cited

U.S. PATENT DOCUMENTS

| | | | |
|---|---|---|---|
| 4,475,972 A | 10/1984 | Wong | |
| 4,580,568 A | 4/1986 | Gianturco | |
| 4,738,740 A | 4/1988 | Pinchuk et al. | |
| 4,743,252 A | 5/1988 | Martin, Jr. et al. | |
| 4,759,757 A | 7/1988 | Pinchuk | |
| 4,776,337 A | 10/1988 | Palmaz | |
| 4,800,882 A | 1/1989 | Gianturco | |
| 4,907,336 A | 3/1990 | Gianturco | |
| 5,015,253 A | 5/1991 | MacGregor | |
| 5,019,090 A | 5/1991 | Pinchuk | |
| 5,041,126 A | 8/1991 | Gianturco | |
| 5,059,211 A | 10/1991 | Stack et al. | |
| 5,102,417 A | 4/1992 | Palmaz | |
| 5,104,404 A | 4/1992 | Wolff | |
| 5,116,360 A | 5/1992 | Pinchuk et al. | |
| 5,122,154 A | 6/1992 | Rhodes | |
| 5,133,732 A | 7/1992 | Wiktor | |
| 5,147,370 A | 9/1992 | McNamara et al. | |
| 5,163,951 A | 11/1992 | Pinchuk et al. | |
| 5,171,262 A | 12/1992 | MacGregor | |
| 5,221,261 A | 6/1993 | Termin et al. | |
| 5,282,823 A | 2/1994 | Schwartz et al. | |
| 5,292,331 A | 3/1994 | Boneau | |
| 5,314,444 A | 5/1994 | Gianturco | |

(Continued)

FOREIGN PATENT DOCUMENTS

CA 2309079 11/2004

(Continued)

OTHER PUBLICATIONS

U.S. Appl. No. 10/909,117, mail date Nov. 17, 2010, Issue Notification.

(Continued)

*Primary Examiner* — David Isabella
*Assistant Examiner* — Andrew Iwamaye
(74) *Attorney, Agent, or Firm* — Workman Nydegger; Jonathan D. Feuchtwang

(57) ABSTRACT

The present invention relates to an endoprosthesis for delivery in a body lumen that includes a plurality of web rings coupled one to the other by flexible connectors, which are structured to absorb at least some of the axial and torsional stresses applied to the endoprosthesis and to improve resistance of the endoprosthesis to clinical fatigue. The connectors are each composed of struts sequentially adjoined one to the other, with foot-shaped extensions protruding at the intersections of pairs of the struts.

16 Claims, 5 Drawing Sheets

U.S. PATENT DOCUMENTS

| | | |
|---|---|---|
| 5,370,683 A | 12/1994 | Fontaine |
| 5,378,239 A | 1/1995 | Termin et al. |
| 5,380,299 A | 1/1995 | Fearnot et al. |
| 5,421,955 A | 6/1995 | Lau et al. |
| 5,443,458 A | 8/1995 | Eury |
| 5,443,496 A | 8/1995 | Schwartz et al. |
| 5,449,373 A | 9/1995 | Pinchasik et al. |
| 5,449,382 A | 9/1995 | Dayton |
| 5,476,508 A | 12/1995 | Amstrup |
| 5,496,277 A | 3/1996 | Termin et al. |
| 5,514,154 A | 5/1996 | Lau et al. |
| 5,527,354 A | 6/1996 | Fontaine et al. |
| 5,556,414 A | 9/1996 | Turi |
| 5,569,295 A | 10/1996 | Lam |
| 5,591,197 A | 1/1997 | Orth et al. |
| 5,591,224 A | 1/1997 | Schwartz et al. |
| 5,593,417 A | 1/1997 | Rhodes |
| 5,593,442 A | 1/1997 | Klein |
| 5,603,721 A | 2/1997 | Lau et al. |
| 5,609,606 A | 3/1997 | O'Boyle |
| 5,628,788 A | 5/1997 | Pinchuk |
| 5,630,829 A | 5/1997 | Lauterjung |
| 5,632,772 A | 5/1997 | Alcime et al. |
| 5,639,278 A | 6/1997 | Dereume et al. |
| 5,649,952 A | 7/1997 | Lam |
| 5,651,174 A | 7/1997 | Schwartz et al. |
| 5,653,747 A | 8/1997 | Dereume |
| 5,670,161 A | 9/1997 | Healy et al. |
| 5,674,242 A | 10/1997 | Phan et al. |
| 5,674,277 A | 10/1997 | Freitag |
| 5,693,085 A | 12/1997 | Buirge et al. |
| 5,695,516 A | 12/1997 | Fischell et al. |
| 5,697,971 A | 12/1997 | Fischell et al. |
| 5,700,285 A | 12/1997 | Myers et al. |
| 5,707,386 A | 1/1998 | Schnepp-Pesch et al. |
| 5,707,388 A | 1/1998 | Lauterjung |
| 5,709,703 A | 1/1998 | Lukic et al. |
| 5,709,713 A | 1/1998 | Evans et al. |
| 5,716,393 A | 2/1998 | Lindenburg et al. |
| 5,723,003 A | 3/1998 | Winston et al. |
| 5,723,004 A | 3/1998 | Dereume et al. |
| 5,728,158 A | 3/1998 | Lau et al. |
| 5,733,303 A | 3/1998 | Israel et al. |
| 5,735,892 A | 4/1998 | Myers et al. |
| 5,735,893 A | 4/1998 | Lau et al. |
| 5,735,897 A | 4/1998 | Buirge |
| 5,738,817 A | 4/1998 | Danforth et al. |
| 5,741,325 A | 4/1998 | Chaikof et al. |
| 5,741,327 A | 4/1998 | Frantzen |
| 5,743,874 A | 4/1998 | Fischell et al. |
| 5,749,880 A | 5/1998 | Banas et al. |
| 5,755,771 A | 5/1998 | Penn et al. |
| 5,755,772 A | 5/1998 | Evans et al. |
| 5,755,774 A | 5/1998 | Pinchuk |
| 5,755,781 A | 5/1998 | Jayaraman |
| 5,769,884 A | 6/1998 | Solovay |
| 5,776,161 A | 7/1998 | Globerman |
| 5,776,181 A | 7/1998 | Lee et al. |
| 5,776,183 A | 7/1998 | Kanesaka et al. |
| 5,782,904 A | 7/1998 | White et al. |
| 5,800,526 A | 9/1998 | Anderson et al. |
| 5,807,404 A | 9/1998 | Richter |
| 5,810,868 A | 9/1998 | Lashinski et al. |
| 5,810,870 A | 9/1998 | Myers et al. |
| 5,810,872 A | 9/1998 | Kanesaka et al. |
| 5,814,063 A | 9/1998 | Freitag |
| 5,817,126 A | 10/1998 | Imran |
| 5,824,037 A | 10/1998 | Fogarty et al. |
| 5,824,045 A | 10/1998 | Alt |
| 5,824,048 A | 10/1998 | Tuch |
| 5,824,054 A | 10/1998 | Khosravi et al. |
| 5,824,059 A | 10/1998 | Wijay |
| 5,827,321 A | 10/1998 | Roubin et al. |
| 5,836,964 A | 11/1998 | Richter et al. |
| 5,836,966 A | 11/1998 | St. Germain |
| 5,843,120 A | 12/1998 | Israel et al. |
| 5,843,158 A | 12/1998 | Lenker et al. |
| 5,843,161 A | 12/1998 | Solovay |
| 5,843,164 A | 12/1998 | Frantzen et al. |
| 5,846,247 A | 12/1998 | Unsworth et al. |
| 5,853,419 A | 12/1998 | Imran |
| 5,855,598 A | 1/1999 | Pinchuk |
| 5,855,600 A | 1/1999 | Alt |
| 5,860,999 A | 1/1999 | Schnepp-Pesch et al. |
| 5,861,027 A | 1/1999 | Trapp |
| 5,868,781 A | 2/1999 | Killion |
| 5,871,538 A | 2/1999 | Dereume |
| 5,876,449 A | 3/1999 | Starck et al. |
| 5,876,450 A | 3/1999 | Johlin, Jr. |
| 5,895,406 A | 4/1999 | Gray et al. |
| 5,897,589 A | 4/1999 | Cottenceau et al. |
| 5,922,021 A | 7/1999 | Jang |
| 5,928,248 A | 7/1999 | Acker |
| 5,938,682 A | 8/1999 | Hojeibane et al. |
| 5,948,018 A | 9/1999 | Dereume et al. |
| 5,954,743 A | 9/1999 | Jang |
| 5,968,091 A | 10/1999 | Pinchuk et al. |
| 5,968,561 A | 10/1999 | Batchelder et al. |
| 5,980,552 A | 11/1999 | Pinchasik et al. |
| 5,984,965 A | 11/1999 | Knapp et al. |
| 6,017,365 A * | 1/2000 | Von Oepen .................. 623/1.15 |
| 6,019,789 A | 2/2000 | Dinh et al. |
| 6,027,526 A | 2/2000 | Limon et al. |
| 6,033,433 A | 3/2000 | Ehr et al. |
| 6,033,434 A | 3/2000 | Borghi |
| 6,033,435 A | 3/2000 | Penn et al. |
| 6,039,756 A | 3/2000 | Jang |
| 6,048,361 A | 4/2000 | Von Oepen |
| 6,059,811 A | 5/2000 | Pinchasik et al. |
| 6,068,656 A | 5/2000 | Von Oepen |
| 6,071,308 A | 6/2000 | Ballou et al. |
| 6,086,610 A | 7/2000 | Duerig et al. |
| 6,099,561 A | 8/2000 | Alt |
| 6,106,548 A | 8/2000 | Roubin et al. |
| 6,113,627 A | 9/2000 | Jang |
| 6,117,165 A | 9/2000 | Becker |
| 6,117,535 A | 9/2000 | Szycher et al. |
| 6,123,721 A * | 9/2000 | Jang ............................ 623/1.15 |
| 6,132,460 A | 10/2000 | Thompson |
| 6,152,957 A | 11/2000 | Jang |
| 6,165,212 A | 12/2000 | Dereume et al. |
| 6,168,409 B1 | 1/2001 | Fare |
| 6,174,326 B1 | 1/2001 | Kitakoa et al. |
| 6,179,868 B1 | 1/2001 | Burpee et al. |
| 6,190,403 B1 | 2/2001 | Fischell et al. |
| 6,193,744 B1 | 2/2001 | Ehr et al. |
| 6,193,747 B1 | 2/2001 | Von Oepen |
| 6,200,334 B1 | 3/2001 | Jang |
| 6,200,335 B1 | 3/2001 | Igaki |
| 6,203,569 B1 | 3/2001 | Wijay |
| 6,231,598 B1 | 5/2001 | Berry et al. |
| 6,231,600 B1 | 5/2001 | Zhong |
| 6,241,762 B1 | 6/2001 | Shanley |
| 6,245,101 B1 | 6/2001 | Drasler et al. |
| 6,253,443 B1 | 7/2001 | Johnson |
| 6,258,116 B1 | 7/2001 | Hojeibane |
| 6,261,318 B1 | 7/2001 | Lee et al. |
| 6,264,688 B1 | 7/2001 | Herklotz et al. |
| 6,264,690 B1 | 7/2001 | Von Oepen |
| 6,270,524 B1 | 8/2001 | Kim |
| 6,273,913 B1 | 8/2001 | Wright et al. |
| 6,299,604 B1 | 10/2001 | Ragheb et al. |
| 6,299,635 B1 | 10/2001 | Frantzen |
| 6,325,825 B1 | 12/2001 | Kula et al. |
| 6,331,189 B1 * | 12/2001 | Wolinsky et al. ............. 623/1.15 |
| 6,332,089 B1 | 12/2001 | Acker et al. |
| 6,340,366 B2 | 1/2002 | Wijay |
| 6,348,065 B1 | 2/2002 | Brown et al. |
| 6,377,835 B1 | 4/2002 | Schoenberg et al. |
| 6,395,020 B1 | 5/2002 | Ley et al. |
| 6,416,539 B1 | 7/2002 | Hassdenteufel |
| 6,436,132 B1 | 8/2002 | Patel et al. |
| 6,443,982 B1 | 9/2002 | Israel et al. |
| 6,451,049 B2 | 9/2002 | Vallana et al. |
| 6,485,508 B1 | 11/2002 | McGuinness |
| 6,488,702 B1 | 12/2002 | Besselink |
| 6,491,718 B1 | 12/2002 | Ahmad |

| | | |
|---|---|---|
| 6,503,272 B2 | 1/2003 | Duerig et al. |
| 6,506,211 B1 | 1/2003 | Skubitz et al. |
| 6,508,834 B1 | 1/2003 | Pinchasik et al. |
| 6,540,776 B2 | 4/2003 | Sanders Millare et al. |
| 6,558,415 B2 | 5/2003 | Thompson |
| 6,572,646 B1 | 6/2003 | Boylan et al. |
| 6,589,276 B2 | 7/2003 | Pinchasik et al. |
| 6,602,285 B1 | 8/2003 | Von Oepen et al. |
| 6,607,554 B2* | 8/2003 | Dang et al. ............ 623/1.15 |
| 6,616,689 B1 | 9/2003 | Ainsworth et al. |
| 6,624,097 B2 | 9/2003 | Martin et al. |
| D481,139 S | 10/2003 | Seibold et al. |
| 6,629,994 B2 | 10/2003 | Gomez et al. |
| 6,652,574 B1 | 11/2003 | Jayaraman |
| 6,679,911 B2 | 1/2004 | Burgermeister |
| 6,682,554 B2* | 1/2004 | Oepen et al. ............ 623/1.15 |
| 6,723,119 B2 | 4/2004 | Pinchasik et al. |
| 6,730,252 B1 | 5/2004 | Teoh et al. |
| 6,740,114 B2 | 5/2004 | Burgermeister |
| 6,749,629 B1 | 6/2004 | Hong et al. |
| 6,755,856 B2 | 6/2004 | Fierens et al. |
| 6,761,733 B2 | 7/2004 | Chobotov et al. |
| 6,770,088 B1 | 8/2004 | Jang |
| 6,776,794 B1 | 8/2004 | Hong et al. |
| 6,786,922 B2 | 9/2004 | Schaeffer |
| 6,790,227 B2 | 9/2004 | Burgermeister |
| 6,796,999 B2 | 9/2004 | Pinchasik |
| 6,821,292 B2 | 11/2004 | Pazienza et al. |
| 6,846,323 B2 | 1/2005 | Yip et al. |
| 6,875,228 B2 | 4/2005 | Pinchasik et al. |
| 6,881,222 B2 | 4/2005 | White et al. |
| 6,913,619 B2 | 7/2005 | Brown et al. |
| 6,916,336 B2* | 7/2005 | Patel et al. ............ 623/1.16 |
| 6,929,660 B1* | 8/2005 | Ainsworth et al. ...... 623/1.15 |
| 6,942,689 B2 | 9/2005 | Majercak |
| 6,955,686 B2 | 10/2005 | Majercak et al. |
| 6,998,060 B2 | 2/2006 | Tomonto |
| 7,029,493 B2 | 4/2006 | Majercak et al. |
| 7,060,093 B2 | 6/2006 | Dang et al. |
| 7,128,756 B2* | 10/2006 | Lowe et al. ............ 623/1.15 |
| 7,141,062 B1 | 11/2006 | Pinchasik et al. |
| 7,179,286 B2 | 2/2007 | Lenz |
| 7,329,277 B2 | 2/2008 | Addonizio et al. |
| 7,520,892 B1* | 4/2009 | Ainsworth et al. ...... 623/1.16 |
| 7,625,398 B2 | 12/2009 | Clifford et al. |
| 7,686,843 B2 | 3/2010 | Moore |
| 7,766,956 B2 | 8/2010 | Jang |
| 2001/0007955 A1 | 7/2001 | Drasler et al. |
| 2001/0027339 A1 | 10/2001 | Boatman et al. |
| 2001/0049549 A1 | 12/2001 | Boylan et al. |
| 2002/0019660 A1 | 2/2002 | Gianotti et al. |
| 2002/0065549 A1 | 5/2002 | White et al. |
| 2002/0107560 A1 | 8/2002 | Richter |
| 2002/0111669 A1* | 8/2002 | Pazienza et al. ......... 623/1.15 |
| 2002/0113331 A1 | 8/2002 | Zhang et al. |
| 2002/0151964 A1 | 10/2002 | Smith et al. |
| 2002/0169499 A1 | 11/2002 | Zilla et al. |
| 2003/0055487 A1* | 3/2003 | Calisse ................. 623/1.15 |
| 2003/0083736 A1 | 5/2003 | Brown et al. |
| 2003/0114918 A1* | 6/2003 | Garrison et al. ......... 623/1.13 |
| 2003/0120334 A1 | 6/2003 | Gerbeding |
| 2004/0051201 A1 | 3/2004 | Greenhalgh et al. |
| 2004/0093073 A1 | 5/2004 | Lowe et al. |
| 2004/0102836 A1 | 5/2004 | Fischell et al. |
| 2004/0126405 A1 | 7/2004 | Sahatjian et al. |
| 2004/0193250 A1 | 9/2004 | Von Oepen et al. |
| 2004/0230293 A1 | 11/2004 | Yip et al. |
| 2004/0236407 A1 | 11/2004 | Fierens et al. |
| 2004/0243220 A1 | 12/2004 | Gianotti et al. |
| 2004/0267353 A1 | 12/2004 | Gregorich |
| 2005/0004650 A1 | 1/2005 | Oepen et al. |
| 2005/0004651 A1 | 1/2005 | Von Oepen et al. |
| 2005/0004658 A1 | 1/2005 | Oepen et al. |
| 2005/0004659 A1 | 1/2005 | Von Oepen et al. |
| 2005/0004662 A1 | 1/2005 | Von Oepen et al. |
| 2005/0043777 A1 | 2/2005 | Von Oepen et al. |
| 2005/0043778 A1 | 2/2005 | Von Oepen et al. |
| 2005/0075716 A1 | 4/2005 | Yan |
| 2005/0222671 A1 | 10/2005 | Schaeffer et al. |
| 2006/0015173 A1 | 1/2006 | Clifford et al. |
| 2006/0106452 A1 | 5/2006 | Niermann |
| 2006/0142844 A1 | 6/2006 | Lowe et al. |
| 2006/0175727 A1 | 8/2006 | Fierens et al. |
| 2006/0184232 A1 | 8/2006 | Gianotti et al. |
| 2006/0206195 A1 | 9/2006 | Calisse |
| 2006/0247759 A1 | 11/2006 | Burpee et al. |
| 2007/0021827 A1 | 1/2007 | Lowe et al. |
| 2007/0021834 A1 | 1/2007 | Young et al. |
| 2007/0135891 A1 | 6/2007 | Schneider |
| 2007/0179593 A1 | 8/2007 | Fierens et al. |
| 2007/0179601 A1 | 8/2007 | Fierens et al. |
| 2007/0213800 A1 | 9/2007 | Fierens et al. |
| 2007/0299505 A1 | 12/2007 | Gregorich et al. |
| 2008/0077231 A1 | 3/2008 | Heringes et al. |
| 2008/0294239 A1 | 11/2008 | Casey |
| 2008/0294240 A1 | 11/2008 | Casey |
| 2009/0163996 A1 | 6/2009 | Bregulla |
| 2009/0163997 A1 | 6/2009 | Casey |
| 2009/0163998 A1 | 6/2009 | Casey |
| 2010/0114297 A1 | 5/2010 | Calisse |
| 2011/0004289 A1 | 1/2011 | Oepen et al. |
| 2012/0165921 A1 | 6/2012 | Casey |

FOREIGN PATENT DOCUMENTS

| | | |
|---|---|---|
| DE | 19840645 | 9/1998 |
| EP | 0357003 | 3/1990 |
| EP | 0221570 | 1/1991 |
| EP | 0699451 | 3/1996 |
| EP | 0709067 | 5/1996 |
| EP | 0808614 | 11/1997 |
| EP | 0815806 | 1/1998 |
| EP | 0928605 | 7/1999 |
| EP | 0950386 | 10/1999 |
| EP | 0983753 | 3/2000 |
| EP | 1042997 | 10/2000 |
| EP | 1095631 | 5/2001 |
| EP | 1516600 | 3/2005 |
| FR | 2774279 | 8/1999 |
| GB | 2344053 | 5/2000 |
| JP | 7-24072 | 1/1995 |
| JP | 08-206226 | 8/1996 |
| JP | 09-010318 | 1/1997 |
| JP | 10-328216 | 12/1998 |
| JP | 11-299901 | 2/1999 |
| JP | 2000312721 | 11/2000 |
| WO | WO91/17789 | 11/1991 |
| WO | WO96/21404 | 7/1996 |
| WO | WO96/25124 | 8/1996 |
| WO | WO97/12563 | 4/1997 |
| WO | WO97/12564 | 4/1997 |
| WO | WO97/14375 | 4/1997 |
| WO | WO98/32412 | 7/1998 |
| WO | WO98/47447 | 10/1998 |
| WO | WO99/07308 | 2/1999 |
| WO | WO99/17680 | 4/1999 |
| WO | WO99/23976 | 5/1999 |
| WO | WO99/38456 | 8/1999 |
| WO | WO99/38458 | 8/1999 |
| WO | WO99/39660 | 8/1999 |
| WO | WO99/39663 | 8/1999 |
| WO | WO99/49928 | 10/1999 |
| WO | 0013611 | 3/2000 |
| WO | WO00/32241 | 6/2000 |
| WO | WO00/45744 | 8/2000 |
| WO | WO00/53119 | 9/2000 |
| WO | WO01/01885 | 1/2001 |
| WO | WO 01/82835 | 11/2001 |
| WO | WO02/26164 | 4/2002 |
| WO | WO02/064061 | 8/2002 |
| WO | WO02/064065 | 8/2002 |
| WO | WO02/094127 | 11/2002 |
| WO | WO03/009779 | 2/2003 |
| WO | WO03/057076 | 7/2003 |
| WO | WO2004/087015 | 10/2004 |
| WO | WO2006/055533 | 5/2006 |
| WO | WO2006/066886 | 6/2006 |
| WO | WO2006/099449 | 9/2006 |
| WO | WO2008/042618 | 4/2008 |

| WO | WO2008/142566 | 11/2008 |
| WO | WO2009/046973 | 4/2009 |
| WO | WO2009/080326 | 7/2009 |
| WO | WO 2009/080327 | 7/2009 |

OTHER PUBLICATIONS

U.S. Appl. No. 11/731,820, mail date Dec. 16, 2010, Notice of Allowance.
U.S. Appl. No. 12/949,481, mail date Jan. 5, 2012, Office Action.
U.S. Appl. No. 12/966,916, mail date Jan. 5, 2012, Office Action.
U.S. Appl. No. 10/903,080, mail date Jan. 26, 2011, Issue Notification.
U.S. Appl. No. 11/601,475, mail date Jan. 26, 2011, Issue Notification.
U.S. Appl. No. 11/961,290, mail date May 6, 2009, Office Action.
U.S. Appl. No. 11/961,290, mail date Dec. 18, 2009, Office Action.
U.S. Appl. No. 11/404,450, mail date Jan. 31, 2012, Office Action.
U.S. Appl. No. 12/895,032, mail date Feb. 1, 2012, Office Action.
U.S. Appl. No. 11/973,707, mail date Feb. 15, 2012, Issue Notification.
U.S. Appl. No. 12/949,481, mail date Feb. 15, 2012, Office Action.
U.S. Appl. No. 12/949,481, filed Nov. 18, 2010, Schneider.
U.S. Appl. No. 10/859,636, mail date Mar. 30, 2011, Issue Notification.
U.S. Appl. No. 11/731,820, mail date Mar. 30, 2011, Issue Notification.
U.S. Appl. No. 13/089,039, filed Apr. 8, 2011, Fierens et al.
U.S. Appl. No. 11/805,584, mail date May 12, 2011, Notice of Allowance.
U.S. Appl. No. 12/966,916, mail date Jun. 10, 2011, Office Action.
U.S. Appl. No. 60/637,495, filed Dec. 20, 2004, Fierens et al.
U.S. Appl. No. 09/582,318, mail date Aug. 14, 2002, Office Action.
U.S. Appl. No. 09/582,318, mail date Mar. 7, 2003, Notice of Allowance.
U.S. Appl. No. 09/742,144, mail date Sep. 24, 2002, Office Action.
U.S. Appl. No. 09/742,144, mail date May 14, 2003, Office Action.
U.S. Appl. No. 09/742,144, mail date Aug. 29, 2003, Notice of Allowance.
U.S. Appl. No. 09/916,394, mail date Aug. 12, 2003, Office Action.
U.S. Appl. No. 09/916,394, mail date Oct. 9, 2003, Office Action.
U.S. Appl. No. 09/916,394, mail date Mar. 2, 2004, Office Action.
U.S. Appl. No. 09/967,789, mail date Sep. 17, 2003, Office Action.
U.S. Appl. No. 09/967,789, mail date Feb. 17, 2004, Notice of Allowance.
U.S. Appl. No. 10/241,523, mail date Aug. 18, 2004, Office Action.
U.S. Appl. No. 10/241,523, mail date Oct. 25, 2004, Office Action.
U.S. Appl. No. 10/241,523, mail date Mar. 8, 2005, Office Action.
U.S. Appl. No. 10/241,523, mail date Jun. 3, 2005, Office Action.
U.S. Appl. No. 10/241,523, mail date Aug. 23, 2005, Office Action.
U.S. Appl. No. 10/241,523, mail date Nov. 16, 2005, Office Action.
U.S. Appl. No. 10/241,523, mail date Apr. 27, 2006, Office Action.
U.S. Appl. No. 10/743,857, mail date Mar. 15, 2007, Office Action.
U.S. Appl. No. 10/743,857, mail date Nov. 16, 2007, Office Action.
U.S. Appl. No. 10/743,857, mail date May 8, 2008, Office Action.
U.S. Appl. No. 10/743,857, mail date Jan. 6, 2009, Office Action.
U.S. Appl. No. 10/743,857, mail date May 27, 2009, Office Action.
U.S. Appl. No. 10/743,857, mail date Feb. 12, 2010, Notice of Allowance.
U.S. Appl. No. 10/743,857, mail date Jun. 25, 2010, Notice of Allowance.
U.S. Appl. No. 10/859,636, mail date Jun. 1, 2007, Office Action.
U.S. Appl. No. 10/859,636, mail date Dec. 31, 2007, Office Action.
U.S. Appl. No. 10/859,636, mail date Apr. 15, 2008, Office Action.
U.S. Appl. No. 10/859,636, mail date Oct. 1, 2008, Notice of Allowance.
U.S. Appl. No. 10/859,636, mail date Mar. 5, 2009, Office Action.
U.S. Appl. No. 10/859,636, mail date Oct. 19, 2009, Notice of Allowance.
U.S. Appl. No. 10/859,636, mail date Feb. 1, 2010, Notice of Allowance.
U.S. Appl. No. 10/859,636, mail date May 19, 2010, Notice of Allowance.
U.S. Appl. No. 10/884,613, mail date Mar. 30, 2005, Office Action.
U.S. Appl. No. 10/884,613, mail date Nov. 14, 2005, Office Action.
U.S. Appl. No. 10/903,013, mail date Mar. 15, 2007, Office Action.
U.S. Appl. No. 10/903,013, mail date Nov. 19, 2007, Office Action.
U.S. Appl. No. 10/903,013, mail date May 14, 2008, Office Action.
U.S. Appl. No. 10/903,013, mail date Jan. 5, 2009, Office Action.
U.S. Appl. No. 10/903,013, mail date May 27, 2009, Office Action.
U.S. Appl. No. 10/903,013, mail date Feb. 12, 2010, Notice of Allowance.
U.S. Appl. No. 10/903,013, mail date Jun. 24, 2010, Notice of Allowance.
U.S. Appl. No. 10/903,014, mail date Mar. 15, 2007, Office Action.
U.S. Appl. No. 10/903,014, mail date Nov. 16, 2007, Office Action.
U.S. Appl. No. 10/903,014, mail date May 13, 2008, Office Action.
U.S. Appl. No. 10/903,014, mail date Jan. 13, 2009, Office Action.
U.S. Appl. No. 10/903,014, mail date Jun. 1, 2009, Office Action.
U.S. Appl. No. 10/903,014, mail date Feb. 5, 2010, Notice of Allowance.
U.S. Appl. No. 10/903,014, mail date May 26, 2010, Office Action.
U.S. Appl. No. 10/903,014, mail date Jun. 24, 2010, Notice of Allowance.
U.S. Appl. No. 10/903,080, mail date Mar. 15, 2007, Office Action.
U.S. Appl. No. 10/903,080, mail date Nov. 19, 2007, Office Action.
U.S. Appl. No. 10/903,080, mail date May 12, 2008, Office Action.
U.S. Appl. No. 10/903,080, mail date Dec. 30, 2008, Office Action.
U.S. Appl. No. 10/903,080, mail date May 27, 2009, Office Action.
U.S. Appl. No. 10/903,080, mail date Jan. 13, 2010, Notice of Allowance.
U.S. Appl. No. 10/909,117, mail date Aug. 22, 2007, Office Action.
U.S. Appl. No. 10/909,117, mail date May 12, 2008, Office Action.
U.S. Appl. No. 10/909,117. mail date Dec. 30, 2008, Office Action.
U.S. Appl. No. 10/909,117, mail date May 27, 2009, Office Action.
U.S. Appl. No. 10/909,117, mail date Jan. 13, 2010, Notice of Allowance.
U.S. Appl. No. 10/909,118, mail date Mar. 29, 2007, Office Action.
U.S. Appl. No. 10/909,118, mail date Nov. 19, 2007, Office Action.
U.S. Appl. No. 10/909,118, mail date May 12, 2008, Office Action.
U.S. Appl. No. 10/909,118, mail date Jan. 5, 2009, Office Action.
U.S. Appl. No. 10/909,118, mail date Jul. 24, 2009, Office Action.
U.S. Appl. No. 10/909,118, mail date Jan. 13, 2010, Notice of Allowance.
U.S. Appl. No. 10/954,948, mail date Mar. 15, 2007, Office Action.
U.S. Appl. No. 10/954,948, mail date Nov. 16, 2007, Office Action.
U.S. Appl. No. 10/954,948, mail date May 15, 2008, Office Action.
U.S. Appl. No. 10/954,948, mail date Jan. 13, 2009, Office Action.
U.S. Appl. No. 10/954,948, mail date May 29, 2009, Office Action.
U.S. Appl. No. 10/954,948, mail date Jan. 13, 2010, Notice of Allowance.
U.S. Appl. No. 10/954,948, mail date Jul. 6, 2010, Notice of Allowance.
U.S. Appl. No. 10/955,425, mail date Mar. 15, 2007, Office Action.
U.S. Appl. No. 10/955,425, mail date Nov. 16, 2007, Office Action.
U.S. Appl. No. 10/955,425, mail date May 13, 2008, Office Action.
U.S. Appl. No. 10/955,425, mail date Jan. 13, 2009, Office Action.
U.S. Appl. No. 10/955,425, mail date May 28, 2009, Office Action.
U.S. Appl. No. 10/955,425, mail date Feb. 26, 2010, Notice of Allowance.
U.S. Appl. No. 10/955,425, mail date Jun. 25, 2010, Notice of Allowance.
U.S. Appl. No. 11/313,110, mail date Jan. 8, 2008, Office Action.
U.S. Appl. No. 11/313,110, mail date Jul. 2, 2008, Office Action.
U.S. Appl. No. 11/313,110, mail date Mar. 3, 2009, Office Action.
U.S. Appl. No. 11/313,110, mail date Nov. 2, 2009, Notice of Allowance.
U.S. Appl. No. 11/313,110, mail date Feb. 18, 2010, Notice of Allowance.
U.S. Appl. No. 11/313,110, mail date Jun. 15, 2010, Notice of Allowance.
U.S. Appl. No. 11/404,450, mail date Feb. 4, 2009, Office Action.
U.S. Appl. No. 11/404,450, mail date Mar. 17, 2009, Office Action.
U.S. Appl. No. 11/404,450, mail date Sep. 30, 2009, Office Action.
U.S. Appl. No. 11/404,450, mail date Apr. 22, 2010, Office Action.
U.S. Appl. No. 11/435,260, mail date Jan. 10, 2008, Office Action.

U.S. Appl. No. 11/435,260, mail date Mar. 26, 2008, Office Action.
U.S. Appl. No. 11/435,260, mail date Dec. 16, 2008, Office Action.
U.S. Appl. No. 11/435,260, mail date Jun. 18, 2009, Notice of Allowance.
U.S. Appl. No. 11/435,260, mail date Jun. 26, 2009, Notice of Allowance.
U.S. Appl. No. 11/601,475, mail date Jul. 22, 2008, Office Action.
U.S. Appl. No. 11/601,475, mail date Jan. 6, 2009, Office Action.
U.S. Appl. No. 11/601,475, mail date Jun. 1, 2009, Office Action.
U.S. Appl. No. 11/601,475, mail date Jan. 15, 2010, Notice of Allowance.
U.S. Appl. No. 11/601,475, mail date Jul. 9, 2010, Notice of Allowance.
U.S. Appl. No. 11/731,820, mail date Jan. 27, 2010, Office Action.
U.S. Appl. No. 11/731,882, mail date Feb. 3, 2010, Office Action.
U.S. Appl. No. 11/732,244, mail date Sep. 28, 2009, Office Action.
U.S. Appl. No. 11/732,244, mail date May 5, 2010, Notice of Allowance.
U.S. Appl. No. 11/732,244, mail date Jun. 21, 2010, Notice of Allowance.
U.S. Appl. No. 11/805,584, mail date Apr. 27, 2009, Office Action.
U.S. Appl. No. 11/805,584, mail date Oct. 29, 2009, Office Action.
U.S. Appl. No. 11/805,584, mail date Mar. 15, 2010, Office Action.
U.S. Appl. No. 11/961,754, mail date Jul. 22, 2009, Office Action.
U.S. Appl. No. 11/961,754, mail date Apr. 5, 2010, Notice of Allowance.
U.S. Appl. No. 11/973,707, mail date Jun. 9, 2009, Office Action.
U.S. Appl. No. 11/973,707, mail date Mar. 19, 2010, Office Action.
U.S. Appl. No. 11/961,775, mail date Oct. 1, 2009, Office Action.
U.S. Appl. No. 11/961,775, mail date Mar. 31, 2010, Office Action.
U.S. Appl. No. 11/404,450, mail date Aug. 10, 2011, Office Action.
U.S. Appl. No. 11/731,882, mail date Aug. 29, 2011, Notice of Allowance.
U.S. Appl. No. 11/805,584, mail date Aug. 24, 2011, Issue Notification.
U.S. Appl. No. 10/743,857, mail date Aug. 18, 2010, Issue Notification.
U.S. Appl. No. 10/903,013, mail date Aug. 18, 2010, Issue Notification.
U.S. Appl. No. 10/903,014, mail date Aug. 25, 2010, Issue Notification.
U.S. Appl. No. 10/903,080, mail date Sep. 16, 2010, Notice of Allowance.
U.S. Appl. No. 10/909,117, mail date Sep. 16, 2010, Notice of Allowance.
U.S. Appl. No. 10/955,425, mail date Sep. 30, 2010, Issue Notification.
U.S. Appl. No. 10/313,110, mail date Sep. 29, 2010, Issue Notification.
U.S. Appl. No. 11/731,820, mail date Aug. 5, 2010, Notice of Allowance.
U.S. Appl. No. 11/731,882, mail date Sep. 1, 2010, Office Action.
U.S. Appl. No. 11/732,244, mail date Sep. 22, 2010, Issue Notification.
U.S. Appl. No. 11/961,754, mail date Jul. 28, 2010, Notice of Allowance.
U.S. Appl. No. 11/973,707, mail date Oct. 12, 2011, Notice of Allowance.
U.S. Appl. No. 12/895,032, filed Sep. 30, 2010, Fierens et al.
U.S. Appl. No. 10/909,118, mail date Sep. 21, 2010, Notice of Allowance.
U.S. Appl. No. 11/805,584, mail date Oct. 4, 2010, Office Action.
U.S. Appl. No. 12/966,916, filed Dec. 13, 2010, Casey.
U.S. Appl. No. 10/859,636, mail date Dec. 9, 2010, Notice of Allowance.
U.S. Appl. No. 11/404,450, mail date Nov. 26, 2010, Office Action.
U.S. Appl. No. 11/961,754, mail date Nov. 23, 2010, Issue Notification.
U.S. Appl. No. 11/731,882, mail date Dec. 14, 2011, Issue Notification.
Landers, Rüdiger and Mülhaupt, Rolf "Desktop manufacturing of complex objects, prototypes and biomedical scaffolds by means of computer-assisted design combined with computer-guided 3D plotting of polymers and reactive oligomers" Macromolecular Materials and Engineering, vol. 282, Issue 1, pp. 17-21, Oct. 2000.
U.S. Appl. No. 12/608,335, mail date May 11, 2012, Office Action.
U.S. Appl. No. 12/875,971, mail date Apr. 19, 2012, Restriction Requirement.
U.S. Appl. No. 12/895,032, mail date Jul. 3, 2012, Office Action.
U.S. Appl. No. 12/966,916, mail date May 23, 2012, Notice of Allowance.
U.S. Appl. No. 11/961,290, mail date Aug. 3, 2012, Office Action.
U.S. Appl. No. 12/875,971, mail date Jul. 26, 2012, Notice of Allowance.
U.S. Appl. No. 12/966,916, mail date Aug. 1, 2012, Issue Notification.
U.S. Appl. No. 12/949,481, filed Aug. 13, 2012, Notice of Allowance.

* cited by examiner

ENDOPROSTHESIS HAVING FLEXIBLE CONNECTORS

FIELD OF THE INVENTION

The present invention relates to an endoprosthesis having elevated axial and torsional flexibility and improved resistance to clinical fatigue. More particularly, the present invention relates to an endoprosthesis having a plurality of web rings coupled by connectors composed of sequentially adjoined struts with foot-shaped extensions protruding from the intersections of pairs of struts.

BACKGROUND OF THE INVENTION

Stents, grafts and a variety of other endoprostheses are well known and used in interventional procedures, such as for treating aneurysms, for lining or repairing vessel walls, for filtering or controlling fluid flow, and for expanding or scaffolding occluded or collapsed vessels. Such endoprostheses can be delivered and used in virtually any accessible body lumen of a human or animal and can be deployed by any of a variety of recognized means.

One type endoprosthesis is the stent, which is employed for the treatment of atherosclerotic stenosis in blood vessels. After a patient undergoes a percutaneous transluminal coronary angioplasty or similar interventional procedure, a stent is often deployed at the treatment site to maintain patency of the vessel. The stent is configured to scaffold or support the treated blood vessel and, if desired, may be loaded with a beneficial agent so as to act as a delivery platform to reduce restenosis or the like.

The endoprosthesis is typically delivered by a catheter delivery system to a desired location or deployment site inside a body lumen of a vessel or other tubular organ. To facilitate such delivery, the endoprosthesis must be capable of having a particularly small crossing profile to access deployment sites within small diameter vessels. Additionally, the intended deployment site may be difficult to access by a physician and often involves traversing the delivery system through the tortuous pathway of the anatomy. Therefore, it would be desirable to provide the endoprosthesis with a sufficient degree of longitudinal flexibility during delivery to allow advancement through the anatomy to the deployed site.

Once deployed, the endoprosthesis should be capable of satisfying a variety of performance characteristics. The endoprosthesis should have sufficient rigidity or outer bias to perform its intended function, such as opening a lumen or supporting a vessel wall. Similarly, the endoprosthesis should have suitable flexibility along its length when deployed so as not to kink or straighten when deployed in a curved vessel. Therefore, it would be desirable for the endoprosthesis to provide substantially uniform or otherwise controlled scaffolding of the vessel wall.

Numerous designs and constructions of various endoprosthesis embodiments have been developed to address one or more of the performance characteristics summarized above. For example, a variety of stent designs are disclosed in the following patents: U.S. Pat. No. 4,580,568 to Gianturco; U.S. Pat. No. 5,102,417 to Palmaz; U.S. Pat. No. 5,104,404 to Wolff; U.S. Pat. No. 5,133,732 to Wiktor; U.S. Pat. No. 5,292,331 to Boneau; U.S. Pat. No. 5,514,154 to Lau et al.; U.S. Pat. No. 5,569,295 to Lam; U.S. Pat. No. 5,707,386 to Schnepp-Pesch et al.; U.S. Pat. No. 5,733,303 to Israel et al.; U.S. Pat. No. 5,755,771 to Penn et al.; U.S. Pat. No. 5,776,161 to Globerman; U.S. Pat. No. 5,895,406 to Gray et al.; U.S. Pat. No. 6,033,434 to Borghi; U.S. Pat. No. 6,099,561 to Alt; U.S. Pat. No. 6,106,548 to Roubin et al.; U.S. Pat. No. 6,113,627 to Jang; U.S. Pat. No. 6,132,460 to Thompson; U.S. Pat. No. 6,331,189 to Wolinsky et al.; and U.S. Pat. No. 7,128,756 to Lowe et al., the entireties of which are incorporated herein by reference.

During use, an endoprosthesis is subjected to a variety of stresses and strains due to compressive, bending and torsional forces applied to the endoprosthesis. Current endoprosthesis designs provide only limited resistance to clinical fatigue, sometimes leading to stent fracture after implantation. This problem is particularly acute for endoprosthesis implanted in body portions that subject the endoprosthesis to severe environments, for example, for stents implants in the superficial femoral artery (SFA). A stent implanted in the SFA is subject to bending and torsional forces after implantation, which may cause the stent to eventually fracture. Not only does a fracture cause a loss of scaffolding properties of the stent and a possible puncture of the vessel, but clinical studies have shown a correlation between stent fracture and restenosis.

Therefore, it would also be desirable to provide an endoprosthesis design that not only provides increased axial and torsional flexibility of the endoprosthesis, but that also offers improved resistance to clinical fatigue.

SUMMARY OF THE INVENTION

The present invention relates to an endoprosthesis for delivery in a body lumen that includes a plurality of web rings coupled one to the other by flexible connectors. Such connectors are structured to absorb at least some of the axial and torsional stresses applied to the endoprosthesis and to improve resistance of the endoprosthesis to clinical fatigue and are each composed of struts sequentially adjoined one to the other, with foot-shaped extensions protruding at the intersections of pairs of the struts.

In one embodiment, an endoprosthesis constructed according to the principles of the present invention includes a web structure expandable from a contracted delivery configuration to an expanded deployed configuration. The web structure is composed of a plurality of longitudinally adjacent web rings, which in turn are defined by a plurality of web elements. The web elements are disposed substantially parallel to the longitudinal axis of the tubular body when the stent is in the contracted delivery configuration, and pairs of the web elements are adjoined one to the other sequentially at junction bends. A connector configured according to the present invention couples a first junction bend in a first web ring to a second junction bend in a second web ring.

The connector of the present invention is formed by a plurality of struts that are joined one to the other at intersections. A foot extension protrudes from at least some of the intersections between the struts, and includes an essentially rectilinear portion that provides the sole portion of the foot extension and an essentially arcuate portion that provides the toe portion of the foot extension.

In one embodiment of the invention, the plurality of struts forming the connectors are disposed transversally in relation to the longitudinal axis of the tubular body, while the sole portions of the foot extensions are disposed essentially parallel to the longitudinal axis. In a preferred embodiment, each connector is formed by three struts and two foot extensions. The first and third struts are disposed at an angle between about 95 and about 115 degrees in relation to the longitudinal axis and the third strut disposed at an angle between about 75 and about 85. A first foot extension couples the first and the second struts, and a second foot extension couples the second and the third struts.

The struts forming the connector may be rectilinear, multi-segment, or curvilinear, and may be of the same length or of different lengths. The foot extension nearer to the first web ring may oriented towards the second web ring and the foot extension nearer to the second web ring may be oriented towards the first web ring, but in different embodiments, the foots extensions may be oriented in other directions.

In a preferred embodiment, the junction bends coupled by a connector are laterally offset one in relation to the other, and less than all junction bends in one web ring are coupled by connectors to junction bends a neighboring ring. In this embodiment, the connectors connecting a first web ring to a second web ring are also laterally offset and oriented symmetrically in relation to the connectors connecting the second web ring to a third web ring. Additionally, each connector may couple the midpoint of a first junction bend to the midpoint of a second junction bends, or couple a first point substantially at one end of a first junction bend to a second point substantially at one end of a second junction bend.

The endoprosthesis of the present invention may also have web rings with web elements of different shapes. In one embodiment, each of the web rings is defined by web elements composed of a central member disposed essentially parallel to the longitudinal axis of the endoprosthesis when in the contracted delivery configuration and coupled at each end to an end member to form a crown profile. The web elements of each web ring are nested one into the other when in the contracted delivery configuration and are oriented at approximately 180 degrees (that is, in opposite directions) in relation to the web elements of the neighboring web ring. In other embodiments, the web elements may have a variety of other configurations.

BRIEF DESCRIPTION OF THE DRAWINGS

The drawings constitute a part of this specification and include exemplary embodiments of the invention, which may be embodied in various forms. It is to be understood that in some instances various aspects of the invention may be shown exaggerated or enlarged to facilitate an understanding of the invention.

DETAILED DESCRIPTION OF EMBODIMENTS OF THE INVENTION

Detailed descriptions of embodiments of the invention are provided herein. It is to be understood, however, that the present invention may be embodied in various forms. Therefore, the specific details disclosed herein are not to be interpreted as limiting, but rather as a representative basis for teaching one skilled in the art how to employ the present invention in virtually any detailed system, structure, or manner.

The present invention relates to an endoprosthesis for delivery within a body lumen that includes a plurality of web rings joined one to the other by connectors configured to provide the endoprosthesis with an elevated degree of axial and torsional flexibility and with increased resistance to clinical fatigue. The endoprosthesis of the present invention may be configured as a stent, graft, valve, occlusive device, trocar, or aneurysm treatment devices and may be adapted for a variety of intralumenal applications, including vascular, coronary, biliary, esophageal, renal, urological, and gastrointestinal.

In its most basic components, the endoprosthesis of the present invention includes a plurality of web rings coupled one to the other by flexible connectors. Such flexible connectors are formed by struts joined sequentially by foot-shaped extensions, which protrude from the intersections of pairs of the struts and which include an essentially rectilinear segment providing the sole portion of the foot extension and an essentially arcuate segment providing the toe portion of the foot extension.

Figure 1:
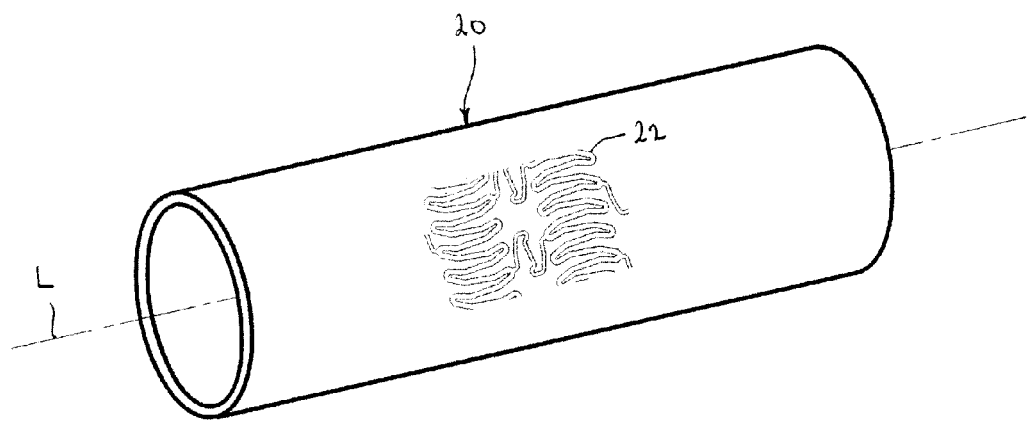
FIG. 1 illustrates a perspective view of an endoprosthesis according to an embodiment of the invention.

Referring to FIG. 1, the endoprosthesis of the present invention may be embodied as a stent 20 having a web structure 22 that is expandable from a contracted configuration to an expanded configuration using techniques known in the art. Typically, stent 20 is disposed on a catheter in the contracted configuration and is delivered to a target location where it is expanded. Expansion of stent 20 may be achieved either by inflating a balloon coupled to the catheter or, if stent 20 is manufactured from a shape memory material such as NITINOL (a nickel-titanium alloy), by allowing stent 20 to self-expand until contact with the lumen wall is established. While stent 20 is depicted in FIG. 1 as having an essentially cylindrical shape, stent 20 may be provided with other shapes, for example, with a frustoconical shape or with the shape of a hyperboloid.

Figure 2:
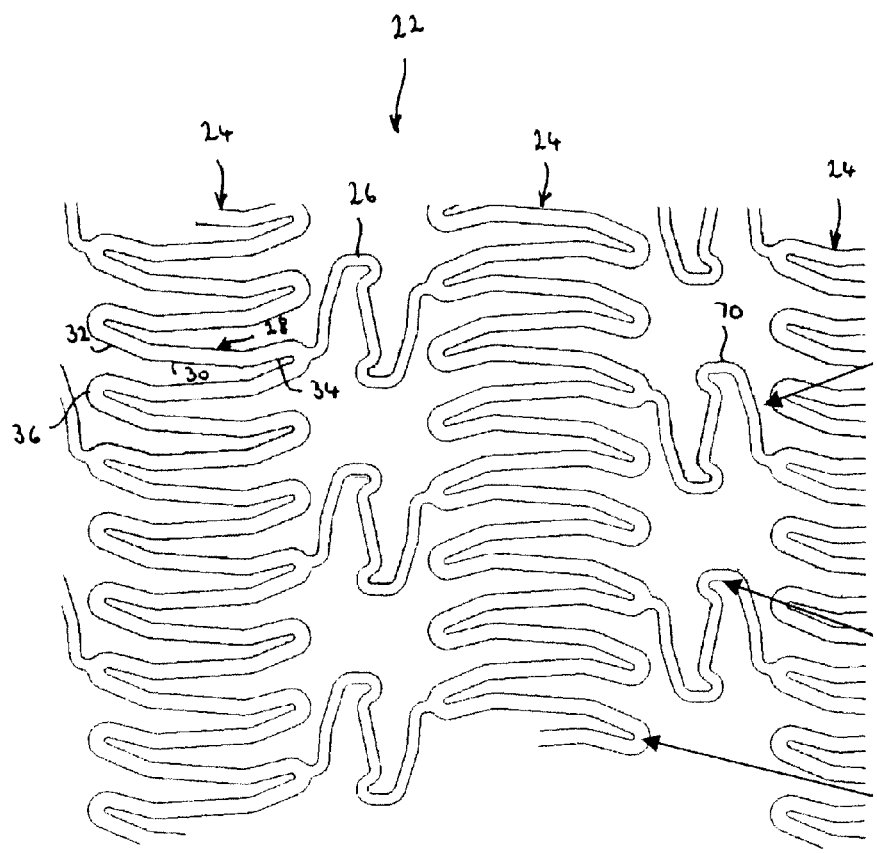
FIG. 2 illustrates a detail view, in flattened form, of the web structure of the embodiment of FIG. 1.

Referring now to FIG. 2, web structure 22 includes a plurality of rings 24 arranged one after the other in the longitudinal direction of stent 20, that is, in a direction parallel to longitudinal axis L of stent 20, and longitudinally coupled one to the other by a plurality of connectors 26.

More particularly, FIG. 2 illustrates web rings 24 in a partially collapsed state. Each of web rings 24 is formed by a plurality of web elements or crowns 28 that are disposed circumferentially around longitudinal axis L and that include a central member 30 and first and second end members 32 and 34 extending respectively from the opposite ends of central member 30. Central member 30 and first and second end members 32 and 34 are each essentially linear in shape, and, when stent 20 is in the contracted delivery configuration, central member 30 is disposed essentially parallel to longitudinal axis L, while first and second members 32 and 34 extend from central member 30 at obtuse angles. Preferably, first and second members 32 and 34 extend from central member 30 at the same angle, but in other embodiments, first and second members 32 and 34 may extend from central member 30 at different angles and may be non-rectilinear in shape.

In the contracted configuration, crowns 28 are nested one into the other and are sequentially adjoined at one end by a junction bend 36 that has an essentially arcuate shape. As shown in FIG. 2, the crowns in one web ring may be disposed with an orientation that is opposite to the orientation of the crowns in a neighboring web ring, in particular, crowns 28 may have an orientation that is 180 degrees different from one web ring 24 to the next. The web rings of the present embodiment are described in U.S. Patent Application Publication Nos. 2004/0193250, 2005/0004651, U.S. Pat. Nos. 6,682,554 and 6,602,285, International Patent Publication No. WO 00/13611, and German Patent Publication No. 19840645, the entireties of which are incorporated herein by reference.

Figure 3:
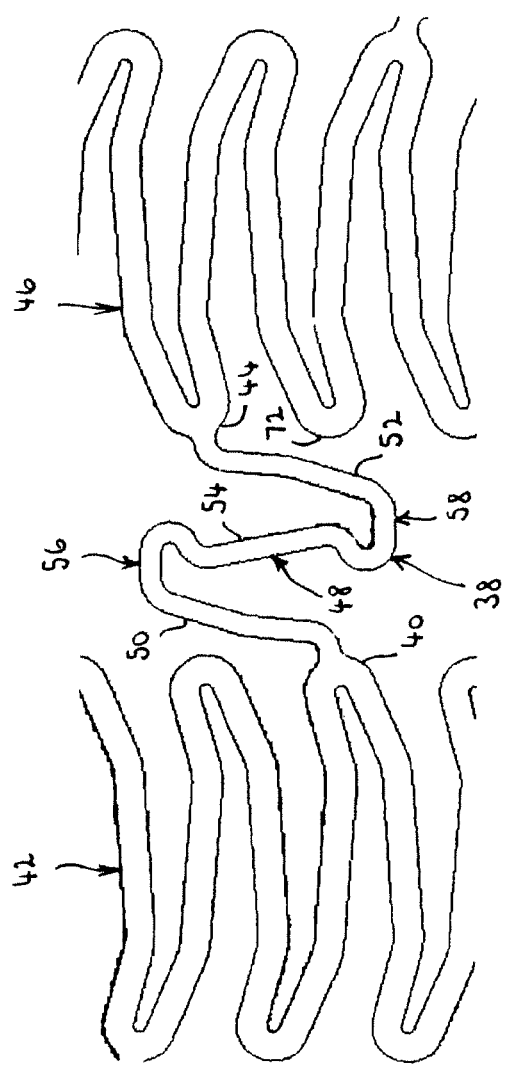
FIG. 3 illustrates a detail view of the web structure of FIG. 2.

Referring now to FIG. 3, a connector 38 constructed according to the principles of the present invention is shown as coupling a first junction bend 40 in a first web ring 42 to a second junction bend 44 in a second web ring 46. Connector 38 is formed by a plurality of struts 48 adjoined sequentially, more particularly, by three struts 48 that are oriented transversally in relation to longitudinal axis L, for example, by struts 50 and 52 oriented at an angle between about 95 and 105 degrees from longitudinal axis L, and by strut 54 oriented at an angle between about 75 and 85 degrees also from longitudinal axis L. A person skilled in the art will appreciate that connector 38 may include more than three struts 48, and that struts 48 may be disposed at different angles in relation to longitudinal axis L. Moreover, struts 50, 52 and 54 may be disposed at different angles one in relation to the other.

Struts 48 may have a rectilinear profile or have a curved profile, or have a profile defined by a plurality of segments. For example, in the embodiment depicted in FIG. 3, strut 54 has having a rectilinear profile and struts 50 and 52 are shown as each having a two-segment profile, with each apex at the intersection of the two segments oriented in the direction of the nearest web ring.

Foot extensions 56 and 58 extend from the intersections between struts 48, and, more particularly, foot extension 56 extends from the intersection between struts 50 and 54, and foot extension extends from the intersection between struts 52 and 54. As shown in the detail view of FIG. 3A related to foot extension 56, but equally applicable to foot extension 58, the foot extension of the present embodiment includes an essentially rectilinear portion extending from strut 50 to provide a sole portion 60, and an arcuate portion connecting sole portion 58 to strut 54 and defining providing a toe portion 62.

Figure 3A:
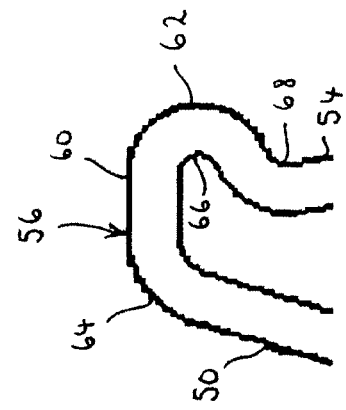
FIG. 3A illustrates a detail view of the connector depicted in FIG. 3.

Also as shown in FIG. 3A, sole portion 60 is coupled to strut 50 with an area of flexure 64, and toe portion 62 is contoured to provide at least two areas of flexure 66 and 68. In different embodiments of the invention, foot extensions 56 and 58 may include straight portions, curved portions or combinations thereof to define an ankle portion, a toe portion, a sole portion and a heel portion. Additionally, sole portion 60 may be a rectilinear segment, as shown in FIG. 3A, or may be contoured as a V-shape, a curved shape, or in a variety of other shapes.

Foot extension 56 may also be provided with a substantially uniform width and thickness throughout. In one variant of the present embodiment, foot extension 56 has an average width greater than the widths of struts 50 and 54, but if foot extension 56 is provided with an increased width, it may be desirable or necessary to distribute stress or eliminate stress concentrations in the pair of converging struts 50 and 54. For example, at least one or both struts 50 and 54 may be provided with a varied width, or one or both of struts 50 and 54 may be tapered from a width substantially similar to or even greater than that of foot extension 56 to a narrower or larger width. A variety of foot extension designs alternative to the embodiment described herein are disclosed in U.S. Pat. No. 7,128,756 to Lowe et al., the entirety of which is incorporated herein by reference.

Because foot extension 56 generally defines areas of flexure 64, 66 and 68 between the pair of struts 50 and 54, a greater axial and torsional stability and a higher longitudinal flexibility are made possible in comparison with stent designs in which foot extension 56 is absent. Therefore, the structure of connector 38 provides for the absorption of at least some of the axial and torsional deformation of web rings 42 and/or 46, and for the distribution of some of the axial and torsional strain outside of crowns 2. These improved properties over the stents in the prior art provide stent 20 with improved clinical resistance to fatigue.

The multiple areas of flexure of foot extension 56 can also compensate for foreshortening upon deployment of stent 20. As web rings 42 and 46 are expanded, foot extension 56 can adjust or compensate for some or all of the change that occurs in the longitudinal dimensions of those web rings. Similarly, foot extension 56 can be stiffened by increasing the width of one or both of the sole and toe portions 60 and 62, or by otherwise altering the geometry of foot extension 56 in a suitable manner, to reduce the amount in which foot extension 56 opens, and thus reduce the extent of related foreshortening that occurs at the connection location.

In the embodiment depicted in FIG. 3, foot extensions 56 and 58 have toe portions oriented inwards and facing each other, that is, the toe portion of foot extension 56 is oriented in the direction of web ring 46 and the toe portion of foot extension 58 is oriented in the direction of web ring 42. In other embodiments of the invention, the toe portions of foot extensions 56 and 58 may be both oriented in the same direction, or may still be oriented in opposite directions but outwards, that is, foot extension 56 would face web ring 42 and foot extension 58 would face web ring 46. In addition, foot extensions 56 and 58 may be oriented in directions not parallel to longitudinal axis L and may be disposed is the same direction or in directions diverging one from the other.

Referring again to FIG. 2, in the illustrated embodiment, not every crown 28 in web ring 24 is coupled to another crown in a neighboring web ring by a connector 26, but only one every three crown 28 is so coupled. A person skilled in the art will appreciate that, in variants of the present embodiment, each crown 28 in one web ring 24 may be coupled to another crown in a neighboring web ring 24, although such design would increase the density of stent 20, correspondingly increasing scaffolding properties in the target location but also decreasing flexibility due to the denser configuration. The above described designs require that the lengths and proportions of struts 48 be dimensioned to achieve the desired nesting among the various connectors 26 when stent 20 is in the contracted delivery configuration.

Connectors 26 coupling a first web ring to a second web rings may not be longitudinally aligned with connectors 70 coupling the second web ring to a third web ring, but instead may be laterally offset one in relation to the other. This arrangement prevents high-density rows of longitudinally aligned connectors from alternating with low-density rows having less material. Instead, the construction of FIG. 2 provides for a more homogenous material distribution along the length of stent 20, which in turn provides for a more homogeneous distribution of stress and strain and reducing the risk of facture. With this configuration, stent 20 can better retain its tubular shape when bent.

Connectors 70 may be oriented symmetrically with respect to connectors 26, more particularly, connectors 70 may be disposed as mirror images of connectors 26, or alternatively connectors 26 and 70 may be disposed in identical directions, that is with struts and foot extensions oriented in the same directions.

Referring now to FIGS. 2 and 3, connectors 26 may not couple junction bends that are longitudinally aligned, but may couple junction bends that are laterally offset one from the other. With specific reference to FIG. 3, connector 56 is shown as coupling not junction bends 40 and 72, which are longitudinally aligned, but instead junction bends 40 and 44 that are laterally offset one from the other. The relative lengths of struts 48 may be adjusted to optimize this offset coupling, for example, central strut 54 mat be longer than struts 50 and 52. The radii and curvatures of the toe portions of foot extensions 56 and 58, and the end portions of connector 38 that provide the physical coupling of connector 38 to junction bends 40 and 44, may also be adjusted to optimize such offset coupling and to maintain, for example, a direction of the sole portions of foot extensions 56 and 58 parallel to longitudinal axis L.

Referring now again to FIGS. 1 and 3, when stent 20 is compressed axially, the offset coupling between junction bends, and, consequently, the offset coupling between the crowns of neighboring web rings 42 and 46 generates a moment that causes a rotational motion of connector 38. Such rotational motion enables connector 38 to engage an adjacent crown when stent 20 is crimped to achieve the contracted delivery configuration, preventing a further compression of the connection segment and improving the deliverability of stent 20.

Figure 4:
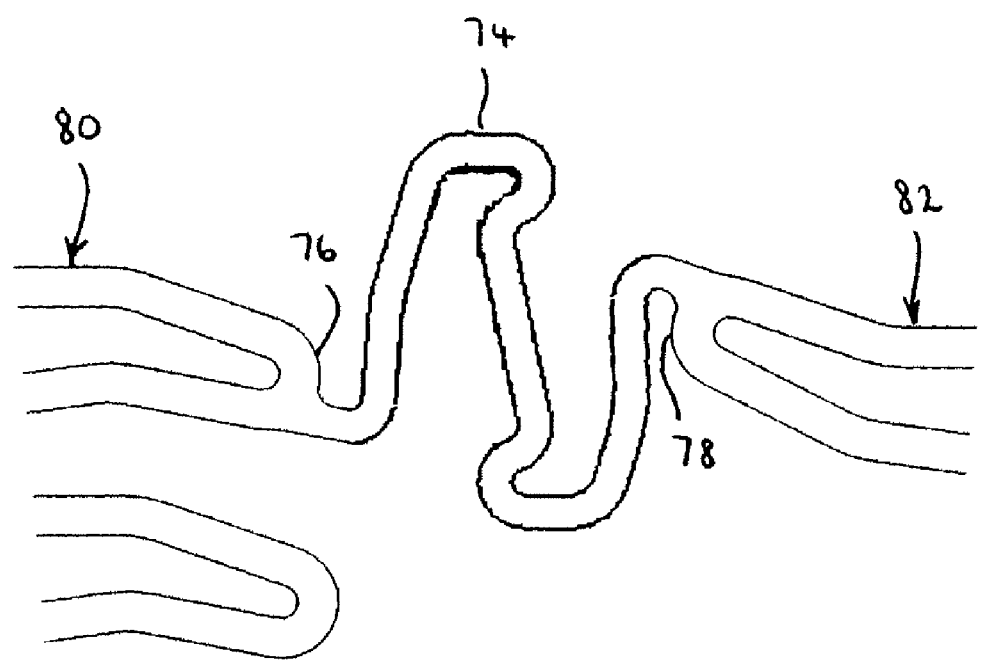
FIG. 4 illustrates a detail view of a variant of the embodiment illustrated of FIG. 3.

FIG. 3 further shows that connector 38 may be coupled to essentially the midpoint of junction bends 40 and 44. In other embodiments of the invention, connector 38 may be coupled to junction bends 40 and 44 at points other than the respective midpoints. For example, FIG. 4 illustrates an embodiment of the invention, in which a connector 74 is coupled to junction bends 76 and 78 near their respective ends so to maximize the distance of the coupling points on junction bends 40 and 44 from a midpoint of connector 74. This arrangement provides for an increase in the moment generated by the offset coupling of web rings 80 and 82 in comparison to the arrangement depicted in FIG. 3. In other embodiments of the invention, connector 26, as generally shown in FIG. 2, may be coupled to still other points in the designated junction bends, for example, to the points closer to a mid-point of connector 26.

Stent 20 may be manufactured from a variety of biocompatible materials, including metal and plastic materials. For example but not by way of limitation, stent 20 may be manufactured from NITINOL (a nickel-titanium alloy) or other shape memory material if a self-expanding configuration of stent 20 is desired, or from stainless steel or a Cobalt Chromium alloy if a balloon expansion is foreseen. Alternatively, stent 20 may be manufactured from a plastic material that enables either a permanent stent placement or a temporary stent placement. For example, stent 20 may be made from a plastic absorbing material.

In some embodiments, crowns 28 and connectors 26 may be manufactured from a biodegradable material when it is expected that only temporary vessel support is required. In another embodiment, only connectors 26 may be manufactured from a biodegradable material, so that the scaffolding provided by stent 20 may change over time by having connectors 26 gradually dissolve in the fluid carried by the vessel (for example, blood), leaving web rings 24 intact so that they may be disposed at specific angles in relation to each other, as required by the patient's anatomy or by the movements of the patient's body.

The embodiments described hereinbefore relate to web elements shaped as crowns 28 of FIG. 2. The connector of the present invention is also applicable to stents having web elements with different designs. For example, FIG. 5 illustrates a flat view of a portion of a web structure 96 formed by a plurality of web rings 84 having web elements 88 shaped differently from crowns 28 and coupled by connectors 86.

Figure 5:
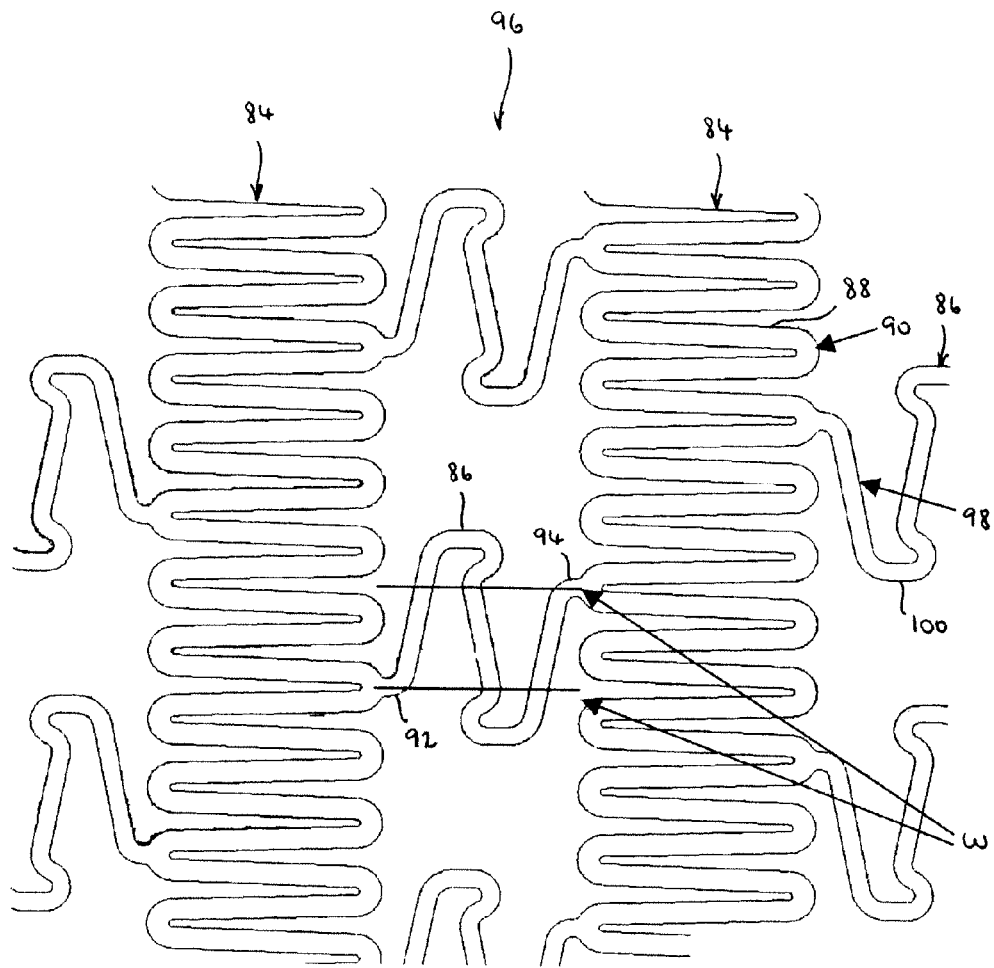
FIG. 5 illustrates a detail view, in flattened form, of a web structure according to another embodiment of the invention.

As shown in FIG. 5, web rings 84 are composed of a plurality of web elements 88 that are each essentially rectilinear and adjoined sequentially by junction bends 90, with junction bends 92 and 94 coupled by connectors 86 being laterally offset by a distance W. The structure and mode of coupling of connectors 86 is the same as previously described with reference to FIGS. 2-4 and will not repeated here for the sake of brevity. Even in this embodiment, connector 86 is still formed by a plurality of struts 98 connected by foot extensions 100.

A person skilled in the art will appreciate that web elements with different shapes may also be employed in constructing the web rings, and that such alternative designs all fall within the spirit and scope of the present invention. A person skilled in the art will also appreciate that the connectors in any of the above described embodiments may be coupled to junction bends with arcuate segments, for example, segments 92 and 94 in FIG. 5, or with segments of different shapes.

While the invention has been described in connection with the above described embodiments, it is not intended to limit the scope of the invention to the particular forms set forth, but on the contrary, it is intended to cover such alternatives, modifications, and equivalents as may be included within the scope of the invention. Further, the scope of the present invention fully encompasses other embodiments that may become obvious to those skilled in the art and the scope of the present invention is limited only by the appended claims.

What is claimed is:

1. An endoprosthesis for delivery in a body lumen comprising:
    a web structure defining tubular body expandable from a contracted delivery configuration to an expanded deployed configuration;
    a plurality of longitudinally adjacent web rings defining the web structure, the longitudinally adjacent web rings being interconnected by a plurality of connector elements;
    a plurality of sequentially adjoined web elements defining each web ring, pairs of the web elements being adjoined at junction bends,
    each of the plurality of connector elements extending between a midpoint of a first junction bend in a first web ring and a midpoint of a second junction bend in an adjacently positioned second web ring, the connector element having a first strut, a second strut, and a third strut, each of the first strut, the second strut, and the third strut being oriented transverse relative to a longitudinal axis of the essentially tubular body, the first strut, the second strut, and the third strut being sequentially adjoined by first and second foot extensions, the first foot extension joining the first strut to the second strut and the second foot extension joining the second strut to the third strut,
    the first and second foot extensions including straight portions disposed lengthwise relative to the longitudinal axis and providing sole portions of the foot extensions and curved portions providing toe portions of the foot extensions, with each toe portion including a contoured portion configured to provide at least two areas of flexure, the contoured portion of the first foot extension including a first curved portion directed toward the second web ring and a second curved portion directed back toward the adjacently positioned first web ring and the contoured portion of the second foot extension including a first curved portion directed toward the first web ring and a second curved portion directed back toward the adjacently positioned second web ring, and
    the first and second toe portions being oriented such that the toe portion of the first foot extension is oriented toward the second web ring and the toe portion of the second foot extension is oriented toward the first web ring.

2. The endoprosthesis of claim 1, one or more of the first and third struts being multi-segment or curvilinear struts.

3. The endoprosthesis of claim 1, the first and the second junction bends being laterally offset one in relation to the other.

4. The endoprosthesis of claim 3, less than all junction bends in the first web ring being connected to another junction bend in the second web ring.

5. The endoprosthesis of claim 4, wherein a plurality of the connector elements connecting the first web ring to the second web ring are laterally offset in relation to a plurality of connector elements connecting the second web ring to an adjacent third web ring.

6. The endoprosthesis of claim 1, the struts being of unequal lengths.

7. The endoprosthesis of claim 1, wherein a plurality of the connector elements disposed between the first and the second web rings are oriented symmetrically in relation to a plurality of connector elements disposed between the second web ring and an adjacent third web ring.

8. The endoprosthesis of claim 1, each of the plurality of connector elements connecting a first point at one end of the first junction bend to a second point at one end of the second junction bend.

9. The endoprosthesis of claim 1, each of the plurality of connector elements being joined to the first and second web rings by first and second bends having arcuate profiles.

10. The endoprosthesis of claim 1,
each of the web elements comprising a central member having a first and a second ends,
the central member being disposed lengthwise relative to the longitudinal axis in the contracted delivery configuration,
the central member being connected at the first end to a first end member at a first obtuse angle, and
the central member being connected at the second end to a second end member at a second obtuse angle.

11. The endoprosthesis of claim 10, the first and the second obtuse angles being equal.

12. The endoprosthesis of claim 11, the web elements of each web ring being nested one into the other in the contracted delivery configuration, and the junction bends having an arcuate shape.

13. The endoprosthesis of claim 11, the plurality of sequentially adjoined web elements in the first web ring being oriented at 180 degrees in relation to the plurality of sequentially adjoined web elements in the second web ring.

14. The endoprosthesis of claim 10, the first and the second obtuse angles being different.

15. The endoprosthesis of claim 1, the web structure being configured to self-expand from the contracted delivery configuration to the expanded deployed configuration.

16. The endoprosthesis of claim 1, the web structure being configured to expand from the contracted delivery configuration to the expanded deployed configuration by application of a radial pressure to an interior surface of the tubular body.

* * * * *